(12) United States Patent
Brockway et al.

(10) Patent No.: US 8,543,195 B1
(45) Date of Patent: Sep. 24, 2013

(54) ECG SENSING WITH NOISE FILTERING

(75) Inventors: Brian Brockway, St. Paul, MN (US);
Marina Brockway, St. Paul, MN (US)

(73) Assignee: VivaQuant, LLC, St. Paul, MN (US)

( * ) Notice: Subject to any disclaimer, the term of this patent is extended or adjusted under 35 U.S.C. 154(b) by 15 days.

(21) Appl. No.: 13/293,632

(22) Filed: Nov. 10, 2011

Related U.S. Application Data

(63) Continuation-in-part of application No. 12/938,995, filed on Nov. 3, 2010.

(60) Provisional application No. 61/412,108, filed on Nov. 10, 2010, provisional application No. 61/257,718, filed on Nov. 3, 2009, provisional application No. 61/366,052, filed on Jul. 20, 2010.

(51) Int. Cl.
*A61B 5/0402* (2006.01)

(52) U.S. Cl.
USPC .......................................... 600/509; 600/300

(58) Field of Classification Search
USPC ........................... 600/300, 508, 509, 522, 523
See application file for complete search history.

(56) References Cited

U.S. PATENT DOCUMENTS

| | | | |
|---|---|---|---|
| 5,090,418 A | 2/1992 | Squires et al. | |
| 5,521,851 A | 5/1996 | Wei et al. | |
| 5,776,073 A * | 7/1998 | Garfield et al. | 600/546 |
| 5,792,065 A | 8/1998 | Xue et al. | |
| 5,817,027 A | 10/1998 | Arand et al. | |
| 5,987,352 A | 11/1999 | Klein et al. | |
| 6,389,308 B1 | 5/2002 | Shusterman | |
| 6,589,189 B2 | 7/2003 | Meyerson et al. | |
| 6,690,959 B2 | 2/2004 | Thompson | |
| 6,701,170 B2 | 3/2004 | Stetson | |
| 6,822,564 B2 | 11/2004 | Al-Ali | |
| 7,099,714 B2 * | 8/2006 | Houben | 600/509 |
| 7,236,819 B2 | 6/2007 | Brockway et al. | |
| 7,272,265 B2 | 9/2007 | Kouri et al. | |
| 7,376,453 B1 | 5/2008 | Diab et al. | |
| 7,602,985 B2 * | 10/2009 | Gao et al. | 382/240 |
| 7,627,369 B2 | 12/2009 | Hunt | |
| 7,672,717 B1 | 3/2010 | Zikov et al. | |
| 7,840,259 B2 | 11/2010 | Xue et al. | |
| 8,271,073 B2 | 9/2012 | Zhang et al. | |
| 2005/0010120 A1 | 1/2005 | Jung et al. | |
| 2005/0234361 A1 | 10/2005 | Holland | |
| 2005/0283090 A1 | 12/2005 | Wells | |
| 2007/0219453 A1 | 9/2007 | Kremliovsky et al. | |
| 2007/0260151 A1 | 11/2007 | Clifford | |

(Continued)

OTHER PUBLICATIONS

G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).

(Continued)

*Primary Examiner* — Brian T Gedeon
(74) *Attorney, Agent, or Firm* — Crawford Maunu PLLC

(57) ABSTRACT

Various embodiments are directed to signal processing. In accordance with example embodiments, methods and apparatuses involve using at least two electrodes that sense an ECG signal. A denoising module is communicatively coupled to the at least two electrodes, and receives the ECG signal sensed by the sensing electrodes. The denoising module includes circuitry that conditions and digitizes the ECG signal, and a computing circuit that processes the digitized ECG signal to denoise the ECG signal. A communications circuit generates a communication including the denoised ECG signal for access by a remote device.

16 Claims, 10 Drawing Sheets

(56) References Cited

U.S. PATENT DOCUMENTS

| | | |
|---|---|---|
| 2007/0265508 A1 | 11/2007 | Sheikhzadeh-Nadjar |
| 2008/0065158 A1 | 3/2008 | Ben-Ezra et al. |
| 2008/0097537 A1 | 4/2008 | Duann et al. |
| 2008/0183093 A1 | 7/2008 | Duann et al. |
| 2008/0200832 A1 | 8/2008 | Stone |
| 2009/0222262 A1 | 9/2009 | Kim et al. |
| 2012/0165691 A1 | 6/2012 | Ting et al. |

OTHER PUBLICATIONS

T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).

D A Clunie, "Extension of an open source DICOM toolkit to support SCP-ECG waveforms," 2nd OpenECG Workshop 2004, Berlin, Germany.

J.-P Martinez, et. al., "A wavelet-based ECG delineator: Evaluation on standard databases," IEEE transactions on biomedical engineering, vol. 51, No. 4, pp. 57 (2004).

Thomsen, M. B., Verduyn, S. C., Stengl, M., Beekman, J. D., de Pater, G., van Opstal, J., et al. (2004). Increased short-term variability of repolarization predicts d- sotalolinduced torsade de pointes in dogs. Circulation, 110, 2453-2459.

Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d.

M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).

S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).

Hamlin RL. Non-drug-related electrocardiographic features in animal models in safety pharmacology. J Pharmacol Toxicol Methods. Jul.-Aug. 2005; 52(1): 60-76.

HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.

R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).

M. Blanco-Velasco, B. Weng and KE Barner, "A New ECG Enhancement Algorithm for Stress ECG Tests," Computers in Cardiology, vol. 33, pp. 917-920 (2006).

Chen PC, Lee S, Kuo CD. Delineation of T-wave in ECG by wavelet transform using multiscale differential operator. IEEE Trans Biomed Eng. Jul. 2006;53(7):1429-33.

K. Zhang, L.-W. Chan, "An Adaptive Method for Subband Decomposition ICA", Neural Computation, vol. 18, No. 1, pp. 191-223 (2006).

R. Brychta, "Wavelet analysis of autonomic and cardiovascular signals," PhD Dissertation. Vanderbilt University (Aug. 2006).

M. Aminghafari, N. Cheze, J.-M Poggi, "Multivariate de-noising using wavelets and principal component analysis," Computational Statistics & Data Analysis, 50, pp. 2381-2398 (2006).

Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).

Chouakri S.A., et al. ECG signal smoothing based on combining wavelet denoising levels. Asian Journal of Information Technology. vol. 5, pp. 667-677. 2006.

Inan, O.T.; Giovangrandi, L.; Kovacs, G.T.A.; Robust Neural-Network-Based Classification of Premature Ventricular Contractions Using Wavelet Transform and Timing Interval Features , IEEE Transactions on Biomedical Engineering vol. 53 , Issue: 12 , , pp. 2507-2515.

L. Smith, A tutorial on Principal Components Analysis.

Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.

K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).

K. Todros and J. Tabrikian, "Blind Separation of Independent Sources Using Gaussian Mixture Model," IEEE Transactions on Signal Processing, vol. 55, No. 7, pp. 3645-3658 (Jul. 2007).

R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).

X. Li, X. Yao, J. Fox, and J. Jefferys, "Interaction Dynamics of Neuronal Oscillations Analysed Using Wavelet Transforms," Journal of Neuroscience Methods 160, pp. 178-185 (2007).

R Schimpf, Ch Antzelevitch, D Haghi, C Giustetto, A Pizzuti, F Gaita, Ch Veltmann, Ch Wolpert, and M Borggrefe. Electromechanical coupling in patients with the short QT syndrome: Further insights into the mechanoelectrical hypothesis of the U wave. Heart Rhythm. Feb. 2008; 5(2): 241-245.

Sarkar S, Ritscher D, Mehra R. A detector for a chronic implantable atrial tachyarrhythmia monitor. IEEE Trans Biomed Eng. Mar. 2008;55(3):1219-24.

M. Malik, K. Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and full-band electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14 , Issue: 2, pp. 152-159.

Dash S, Chon Kh, Lu S, Raeder EA. Automatic real time detection of atrial fibrillation. Ann Biomed Eng. Sep. 2009;37(9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement-Driven Nanogenerator," Nano Letters, vol. 9, No. 3, pp. 1201-1205 (2009).

J. Piccini, et al, Predictors of sudden cardiac death change with time after myocardial infarction: results from the VALIANT trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S. Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg.

http://www.physionet.org/physiobank/database/mitdb/.

B. Widrow, et al., "Adaptive noise cancelling: principles and applications," IEEE Proc., vol. 63, No. 12, pp. 1692-1716, Dec. 1975.

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic (1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution,"Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J. Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A. Hyvärinen, "New Approximations of Differential Entropy for Independent Component Analysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres- Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J-F. Cardoso, "High-Order Contrasts for Independent Component Analysis," Neural Comput., vol. 11, No. 1, pp. 157-192 (1999).

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger AL et al. PhysioBank, PhysioToolkit, and PhysioNet: components of a new research resource for complex physiologic signals. Circulation 101(23): e215-e220, (Jun. 13, 2000).

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

L. K. Saul and J. B. Allen, "Periodic component analysis: An eigenvalue method for representing periodic structure in speech," in NIPS, [Online]., pp. 807-813 (2000). Available: http://www.cs.cmu.edu/Groups/NIPS/00papers-pub-on-web/SaulAllen.pdf.

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, (Mar. 2001).

M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, p(s): 819-823 vol. 1.

M. Costa, A. L. Goldberger, and C.-K. Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

* cited by examiner

ECG SENSING WITH NOISE FILTERING

RELATED PATENT DOCUMENTS

This patent document claims the benefit under 35 U.S.C. §119 of U.S. Provisional Patent Application Ser. No. 61/412,108, filed on Nov. 10, 2010; this patent document is also a continuation-in-part of U.S. patent application Ser. No. 12/938,995, filed on Nov. 3, 2010 and which claims the benefit of U.S. Provisional Patent Application Ser. No. 61/257,718, filed on Nov. 3, 2009, and of U.S. Provisional Patent Application Ser. No. 61/366,052, filed on Jul. 20, 2010, to all of which priority is claimed via 35 U.S.C. §120 for common subject matter; each of these patent documents is fully incorporated herein by reference.

FIELD OF INVENTION

Various aspects of the present invention relate to ECG sensing, and more particular aspects relate to an ECG sensing lead having an active electronic module that removes in-band noise from a sensed ECG signal.

BACKGROUND

In-band noise from EMG and other sources is an obstacle to the extraction of accurate, reliable, and repeatable information from ambulatory ECG recordings. This issue is prevalent in multiple applications where ambulatory monitoring is used including diagnosis and management of patients at risk of cardiac arrhythmias and preclinical and clinical evaluation of drug safety and effectiveness.

Ambulatory ECG monitoring devices often incorporate the ability to detect arrhythmic events and store the ECG strip containing the event for later communication to a computerized system for further review. ECG strips detected by the ambulatory monitoring device as containing an arrhythmia are communicated to a computerized system where the strips containing the events are subjected to further analysis and are evaluated to screen out inaccurate and erroneous information. Other ambulatory devices record the ECG continuously or at regular intervals and the ECG is communicated to a computerized system where intervals are measured and events are detected. Whether the ECGs are analyzed within the ambulatory monitoring device, at a computerized system located in an office, laboratory, or center dedicated to ECG analysis, or a combination thereof, noise can render the ECGs uninterpretable or very difficult to interpret and cause analysis algorithms to produce large numbers of false positive events and errors in interval measurements, requiring manual over-read of the results. This increases labor costs and risks introducing human error, leading to inferior information. For preclinical and clinical drug safety studies, where intervals and arrhythmias are often documented during analysis, noise introduces variability that increases the sample size necessary to reach statistical significance and creates false positives and errors that require expensive manual over-read. These and other matters present challenges to ECG monitoring.

SUMMARY

Various aspects of the present invention are directed to devices, methods, and systems for removing in-band noise from ECG signals (denoising the ECG) sensed on or near the skin surface, prior to recording on an ambulatory monitoring device and in a manner that addresses challenges, including those discussed above.

According to an example embodiment, a denoising module for removing in-band noise of an ECG signal is incorporated into an ECG sensing lead. The complete lead includes at least two connectors located on the distal end of the lead that conductively connect to surface electrodes on or near the skin of a patient, a first lead body conductively connecting the signal sensed by the surface electrodes to the module, the denoising module, and a second lead body conductively connecting the module to a connector on the proximal end of the lead. The connector on the proximal end of the lead plugs into a mating connector on the ambulatory monitoring device. This active ECG sensing lead with integral denoising module provides a denoised ECG signal with output levels compatible with ambulatory monitoring devices and can be used as a replacement for standard passive ECG leads that are used to connect ECG sensing electrodes to an ambulatory monitor.

In one aspect of the present invention, connecting snaps that mate with the skin surface electrodes are connected to the module using wires. The sensed ECG signals are conditioned and digitized and are then processed by a logic circuit or computer processor configured to execute an algorithm for removing in-band noise. The denoised ECG signals are then converted back to low-level analog signals compatible with ambulatory monitoring devices. A second lead body conductively connects the denoised ECG signal from the module to a connector that plugs into the ambulatory monitoring device. In another aspect of this invention, the second lead body is eliminated and the module contains an integral connector that plugs into the ambulatory monitoring device for conductively communicating the denoised ECG signal to the ambulatory monitoring device.

In one aspect of the present invention, an algorithm for removing in-band noise employs adaptive filtering. In another aspect of this invention, the algorithm for removing in-band noise employs a decomposition and thresholding technique. In another aspect of the present invention, the algorithm for removing in-band noise employs multi-domain signal processing techniques. In yet another aspect of the present invention, the ECG signal is comprised of two or more channels and the algorithm for removing in-band noise employs principal component analysis.

BRIEF DESCRIPTION OF THE DRAWINGS

The invention may be more completely understood in consideration of the following detailed description of various embodiments of the invention in connection with accompanying drawings, in which.

Figure 1:
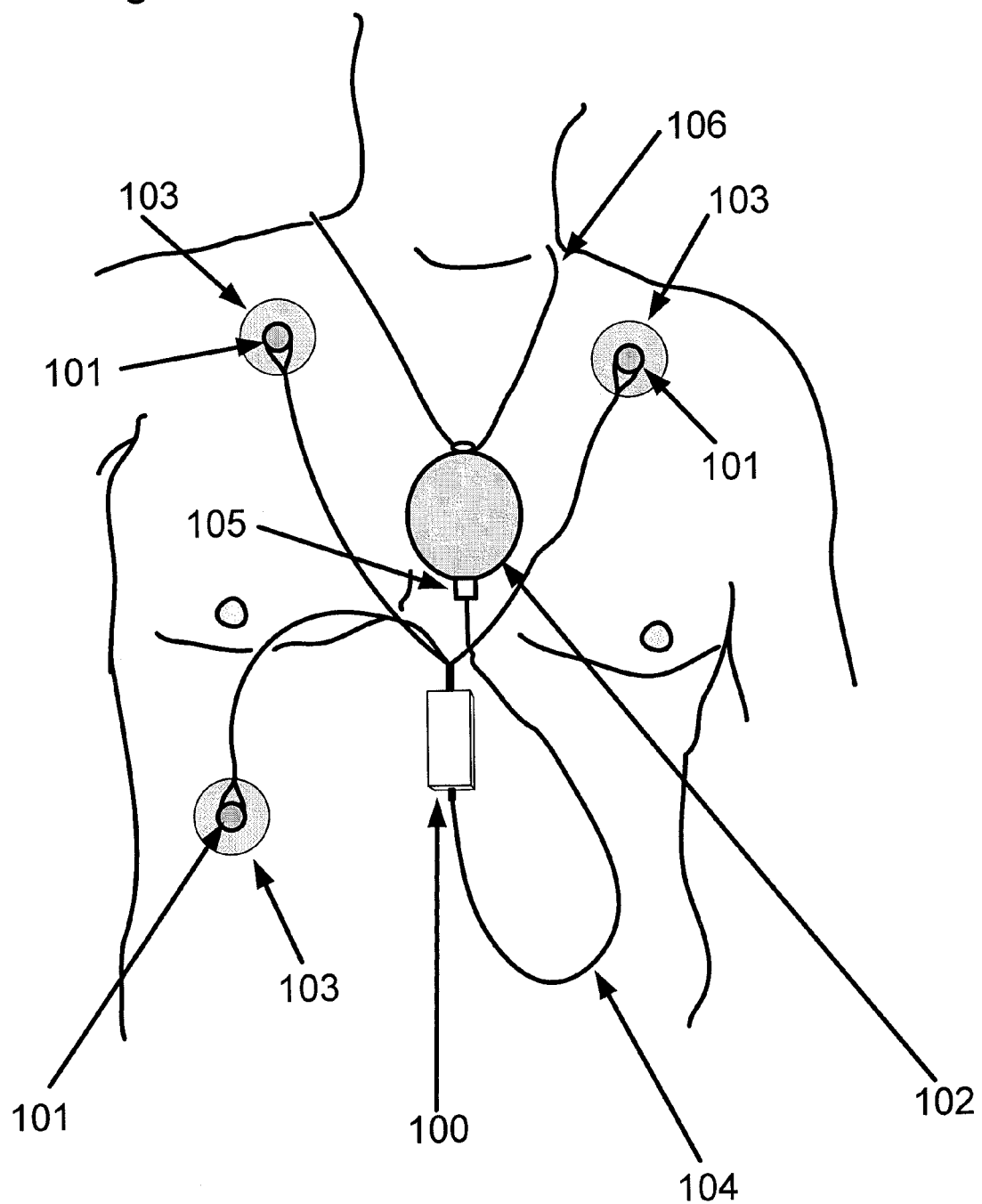
FIG. 1 shows a subject wearing an ambulatory monitoring device employing an ECG lead with integral denoising module, consistent with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

Various example embodiments of the present invention relate to an active lead for sensing an ECG at or near the surface of the body of a subject, removing in-band noise from the sensed ECG, and providing a denoised output signal similar in amplitude to the sensed ECG signal. The active ECG sensing lead with denoising capability, which is the subject invention, can be used with a large installed base of ambulatory monitoring devices already in existence and can be substituted for commonly used passive sensing leads. While the present invention is not necessarily limited to such applications, various aspects of the invention may be appreciated through a discussion of examples using this context.

Certain embodiments of the present invention describe the use of Multi-Domain Filtering (MDF). The term MDF is used herein to refer to embodiments that use Multi-Domain Signal Processing (MDSP) to denoise an ECG signal. Various embodiments of the present invention are directed to denoising ECG signals sensed at the surface of the body of a human being or animal In the context of this invention, denoising refers to removing in-band noise, or noise present within the bandwidth of the ECG signal.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

According to an example embodiment, and referring to FIG. 1, skin electrodes 103 are positioned on the chest of a body surface of a subject to be monitored, sense an ECG signal and are electrically connected to conductive wires via snaps 101. In this embodiment, there are three skin electrodes used to provide two ECG signals (two channels). In an alternate embodiment, two electrodes are placed on the skin of the patient to provide a single channel ECG signal. In yet other alternate embodiments, additional skin electrodes and corresponding conductive wires can be added to provide additional ECG signal channels. The conductive wires extend from each snap to a point of convergence where they consolidate into a lead body that connects to denoising module 100. Denoising module 100 outputs a low-level analog signal of an amplitude similar to the ECG signal sensed by skin electrodes 103. The output signal is conductively communicated by lead body 104 to connector 105 that plugs into ambulatory monitoring device 102 worn by the subject. In this embodiment, ambulatory monitoring device 102 is suspended from lanyard 106 worn around the neck of the monitored subject. In alternate embodiments, skin electrodes may be adhesive backed electrodes such as 3M (St. Paul, Minn.) Red Dot electrodes. Alternately, the skin electrodes may be dry electrodes in direct contact with surface tissue and incorporated into an elastic strap worn around the subject's thorax, such as from Polar Electro (Kempele, Finland). Alternately, the skin electrodes may be dry electrodes positioned or woven into the fabric of a garment worn by the subject and designed to be in contact with the subject's skin such as is available from Textronic, Inc. (Wilmington, Del.). In one embodiment, a garment has multiple ECG electrodes incorporated into the fabric, each electrically connected to the denoising module. The denoising module could be incorporated into a small pouch in the fabric with a lead body extending from the denoising module for connection to an ambulatory monitoring device. In some embodiments the denoising module can be wirelessly connected to a monitoring device such as a heart rate monitor. Alternately, the skin electrodes may be capacitive sensing electrodes such as those described in [1]. In an embodiment that employs capacitive sensing electrodes, additional signal conditioning circuitry can be used to convert the capacitance modulated signal to a voltage representing the ECG signal for input to denoising module 100.

Figure 2:
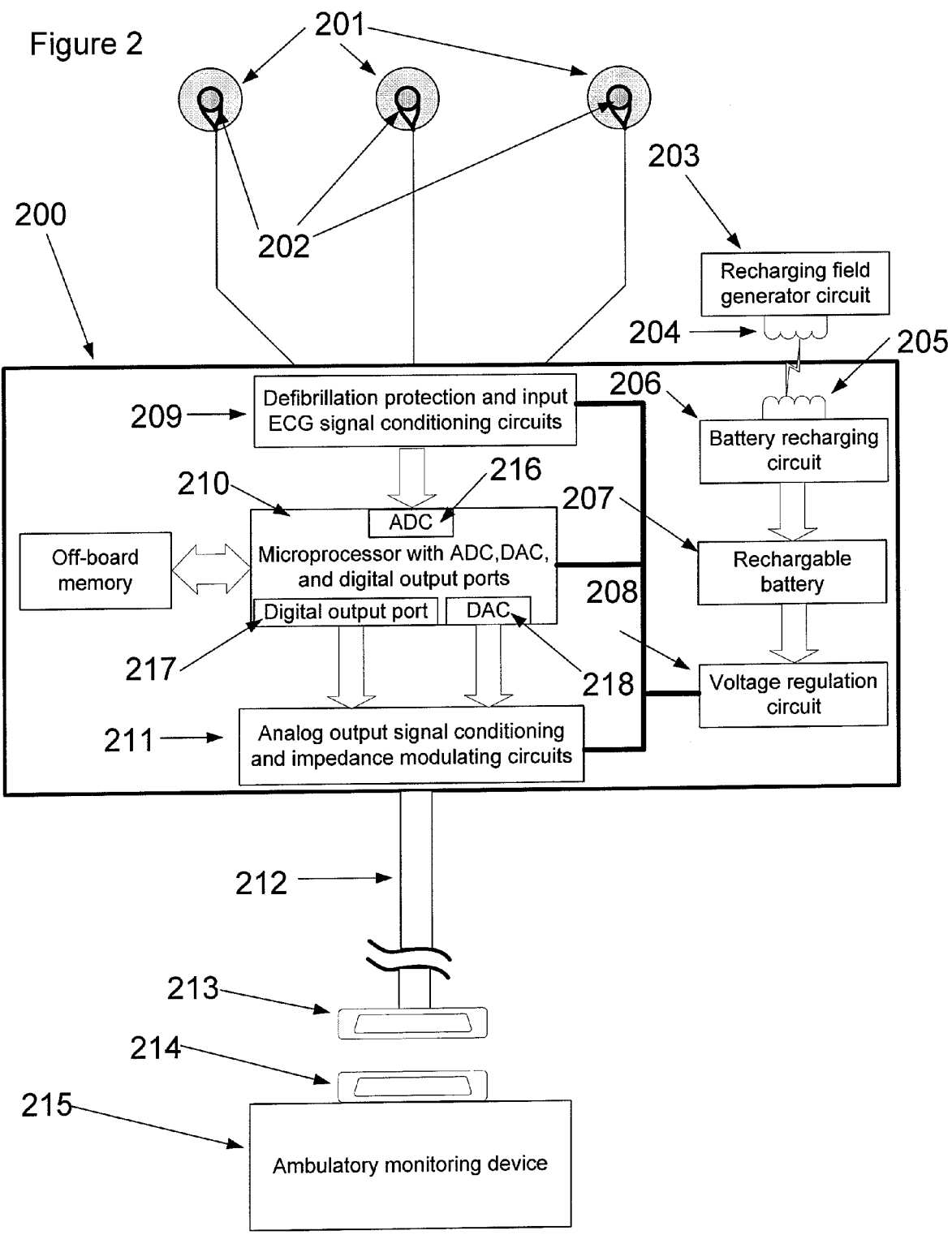
FIG. 2 shows a block diagram of the sensing lead and functional components of a denoising module; consistent with an example embodiment of the present invention.

Referring to FIG. 2, skin electrodes 201 are conductively connected to denoising module 200 by snaps 202 attached to lead wires. Signal conditioning and defibrillation protection circuits 209 protect the electronics from damage in the event the patient is defibrillated as well as amplify the sensed ECG signal. In some embodiments, the circuits 209 may include an anti-aliasing filter that removes energy from the signal outside the band of the frequencies contained in the ECG signal.

In one embodiment, the device shown in FIG. 2 is implemented for monitoring a human ECG, and the amplifier circuits in 209 increase the amplitude of the sensed ECG by a factor of 1,000 from 2.5 mV to 2.5 Volts peak-to-peak and will pass frequencies from 0.05 Hz to 100 Hz. In another embodiment, the device shown in FIG. 2 is used to monitor other species, and the gain and filter settings are different than those used for a human ECG.

The conditioned ECG signal is digitized using an analog-to-digital converter (ADC) 216 in microprocessor chip 210. In one embodiment, chip 210 is a Texas Instruments (Dallas, Tex.) MSP-430 microcontroller. A 16-bit RISC processor executes algorithms to remove in-band noise. The denoised ECG signal is converted to an analog signal via digital-to-analog converter (DAC) 218 incorporated in chip 210. In some embodiments, ADC 216 and DAC 218 may be separate from microprocessor chip 210. The analog output signal is conditioned in circuit 211 to provide filtering and any signal level adjustments necessary to provide compatibility with ambulatory monitoring device 215. The analog output signal is conductively communicated to connector 213 via lead body 212. Connector 213 mates with connector 214 of ambulatory monitoring device 215.

In one embodiment of the present invention, and referring to FIG. 2, an automatic amplitude control (AAC) function can be implemented in chip 210. The AAC attempts to maintain relatively constant QRS complex amplitude. This approach is useful, for example, when used with ambulatory monitoring devices 215 having limitations in QRS detection algorithm where changes in amplitude can be detrimental to performance.

In some embodiments, ambulatory monitoring device 215 is configured to evaluate the integrity of the conductive coupling between skin electrodes 201 and the skin of the subject. This is performed by circuits within device 215 that measure impedance between skin electrodes 201. When an impedance level indicative of poor coupling is detected, device 215 may notify the subject of a problem via an alarm. It is therefore useful for this active sensing lead to detect poor quality ECG signals and modulate an impedance measured by device 215 when poor quality ECG signals are detected. In some embodiments, an algorithm implemented by microprocessor 210 monitors the quality of the signal sensed by skin electrodes 201. If skin electrodes 201 are not making adequate contact with the skin or the skin has not been properly prepared, or the electrodes have not been properly positioned, the signal quality may be poor. When the microprocessor 210 detects that signal quality is unacceptable, it sends a logic level signal to circuit 211 via digital output port 217 to modulate an impedance that is evaluated by ambulatory monitoring device 215. The impedance can be modulated, for example, by switching a high-value resistor in series with an analog signal line carrying the denoised ECG signal to ambulatory monitoring device 215. The switch used to insert the series resistor is activated by a logic-level signal provided from chip 210 via digital output port 217 when the algorithm has detected a poor quality signal.

In some embodiments, denoising module 200 is powered by a primary cell battery that can be replaced via an access in the housing of module. In some embodiments, denoising module 200 is contained in a sealed housing. This may be useful in preventing ingress of moisture that may negatively impact the reliability of the denoising module. For embodiments where the housing of denoising module 200 is sealed, it is useful to use a rechargeable battery such as lithium ion battery or thin film battery. In this embodiment, battery 207 is recharged by recharging circuit 206. Circuit 206 includes inductor 205 to receive a varying magnetic field induced by inductor 204. Circuit 206 processes the alternating voltage produced by inductor 205 and converts it to a direct current suitable for charging battery 207. Recharging field generator circuit 203 provides a varying voltage to inductor 204 to produce the varying magnetic field. It is anticipated that inductor 204 will be placed near or directly adjacent to the location of inductor 205 in order to facilitate a faster charge time for battery 207. In some embodiments, it is anticipated that the charge time for battery 207 will be a few hours and that charging will be required every 1 to 4 weeks. Power regulation circuits 208 regulate the voltage to circuits 209 and 211 and to microprocessor 210. In another embodiment a supercapacitor capable of storing a large amount of charge is used to power the denoising module 200 (e.g., as an alternative to the battery 207).

Figure 3:
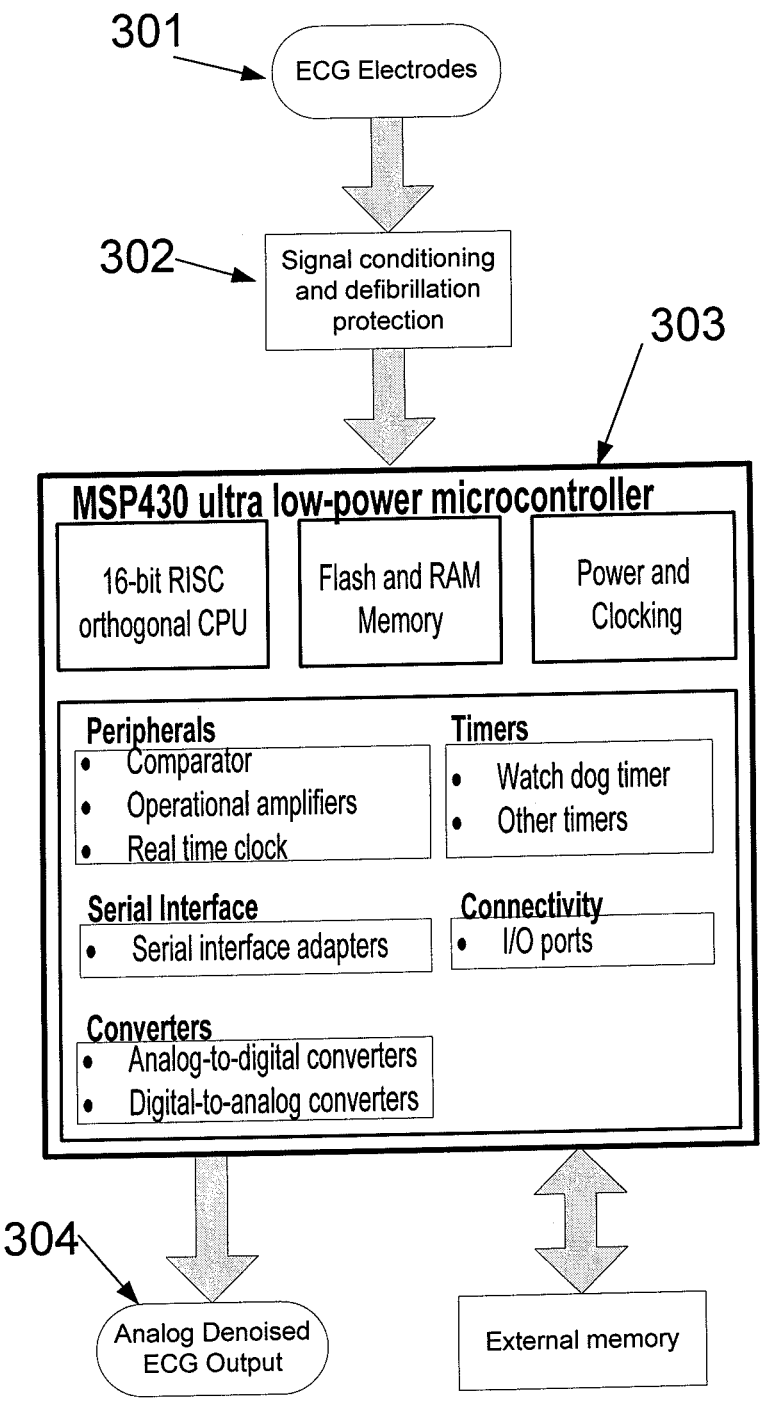
FIG. 3 shows a block diagram of portions of a denoising module, consistent with an example embodiment of the present invention.
Figure 4:
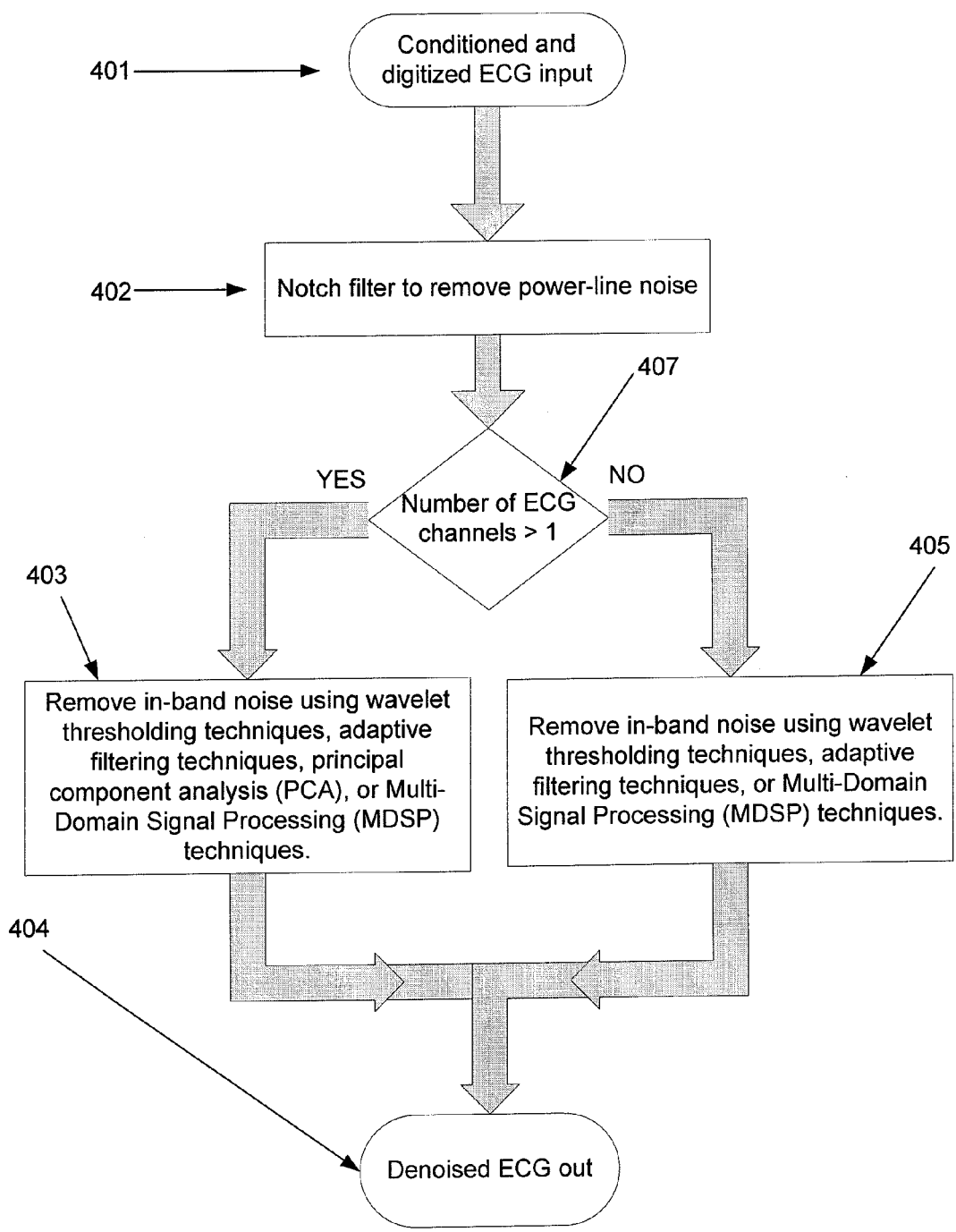
FIG. 4 shows a high-level signal flow diagram of a denoising module, consistent with an example embodiment of the present invention.

Referring to FIG. 3, the sensed ECG signal from electrodes 301 is conditioned by circuits 302 as described herein. The microprocessor 303 executes an algorithm to remove noise from the input ECG signal. Each input channel of the conditioned ECG signal is digitized by an analog-to-digital converter incorporated on the Texas Instruments (Dallas, Tex.) MSP-430 microcontroller chip. In some embodiments, and referring to FIG. 4, the digitized signal 401 is first processed to remove power line noise (e.g. either 60 Hz or 50 Hz, depending upon power line frequency used in individual country) using notch filter 402. In one embodiment, notch filter 402 is implemented using infinite impulse response (IIR) filtering techniques. In other embodiments, power line noise is removed by the denoising process executed by microprocessor 303 in process 403 or 405. In one embodiment, referring to FIG. 4, the possible algorithms used for denoising depends upon the number of channels in the ECG signal. If there is only one channel, denoising is directed by decision point 407 to process 405 and is accomplished using one of adaptive filtering, decomposition and thresholding, and Multi-Domain Signal Processing (MDSP). If there is more than one channel, denoising is directed by decision point 407 to process 403 and is accomplished using one of principal component analysis, adaptive filtering, decomposition and thresholding, and Multi-Domain Signal Processing (MDSP). Following denoising the signal is converted to an analog signal using a digital-to-analog converter at 404.

Figure 5:
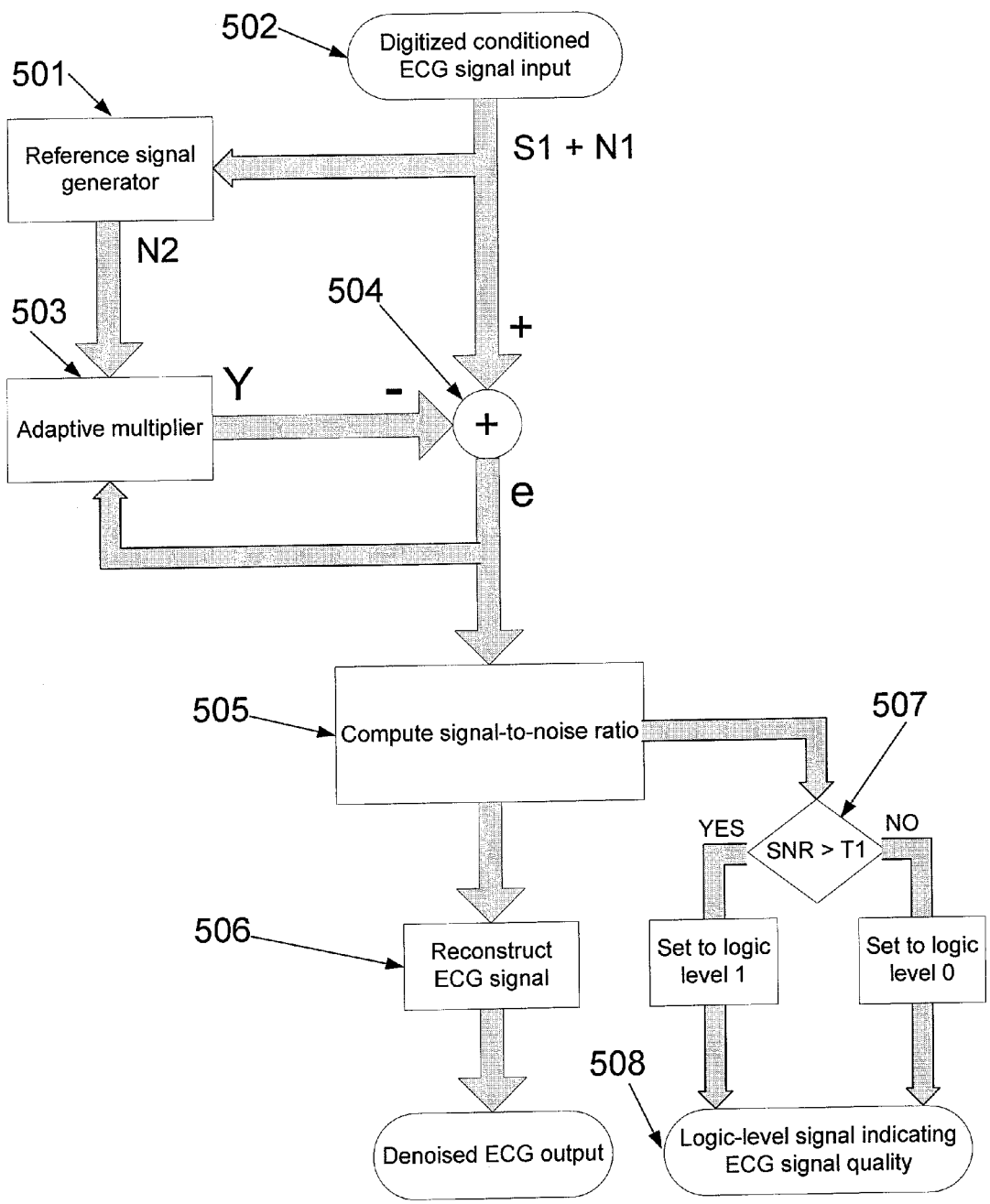
FIG. 5 shows a signal flow diagram of an adaptive filtering denoising algorithm as implemented in a denoising module, consistent with an example embodiment of the present invention.

In one embodiment, and referring to FIG. 5, the digitized ECG signal 502 is denoised using adaptive filtering techniques [4, 5]. The input ECG signal 502 is composed of a desired signal S1 that is corrupted with noise N1. Signal 502 is preprocessed to extract a noise reference signal N2 using reference generator 501. Noise reference signal N2 is correlated with noise signal N1. The adaptive filter algorithm estimates and updates the parameters of adaptive multiplier 503 to minimize the least squared error between the output Y of adaptive multiplier 503 and input signal 502. Summation node 504 computes the difference between the input signal 502 and the output of adaptive multiplier 503. The resulting difference signal e is an estimate of the desired signal S1 when the least squared error between the output Y of 503 and input signal 502 is minimized.

In another embodiment reference signal N2 is acquired independently by a skin electrode, separate from the skin electrodes that produced input signal 502, rather than generating a reference signal from the input signal 502. When the reference signal N2 is a sensed ECG signal S1 is extracted by minimizing mean square error between input signal 502 and the reference signal N2. Examples of techniques that minimize mean square error include least-mean squares, normalized least mean squares, recursive least squares, adaptive recurrent filter, fast affine projection, and fast Euclidean direction [6].

In the process 505, the output signal Y of adaptive multiplier 503 is used as an estimate of noise for computing noise power and the denoised signal e output from summation node 504 is used to compute signal power. The SNR is then computed in process 505 according to formula:

$$SNR_{dB} = 10\log_{10}\left(\frac{P_{signal}}{P_{noise}}\right) \quad (1)$$

where $P_{signal}$ and $P_{noise}$ are respective signal and noise energy. SNR is used to evaluate input signal quality. For example, if a skin electrode is not properly attached, the quality will be poor and would result in a low SNR value. SNR is evaluated relative to a predetermined threshold T1 in decision point 507. A logic-level 0 signal is generated in process 508 if SNR <T1 to signal to circuit 211 of FIG. 2 that a resistor should be inserted into the analog signal line in communication with ambulatory monitoring device 215. Insertion of the resistor effectively increases source impedance in the ECG signal line to ambulatory monitoring device 215, thereby emulating the situation of an increase in source impedance that would occur if a skin electrode of a passive lead were to have come loose. If the ambulatory monitoring device incorporates a mechanism based upon source impedance to signal to the subject that a lead has come loose, it will generate an alarm signal to that effect, as described herein. ECG signals are reconstructed at 506.

Figure 6:
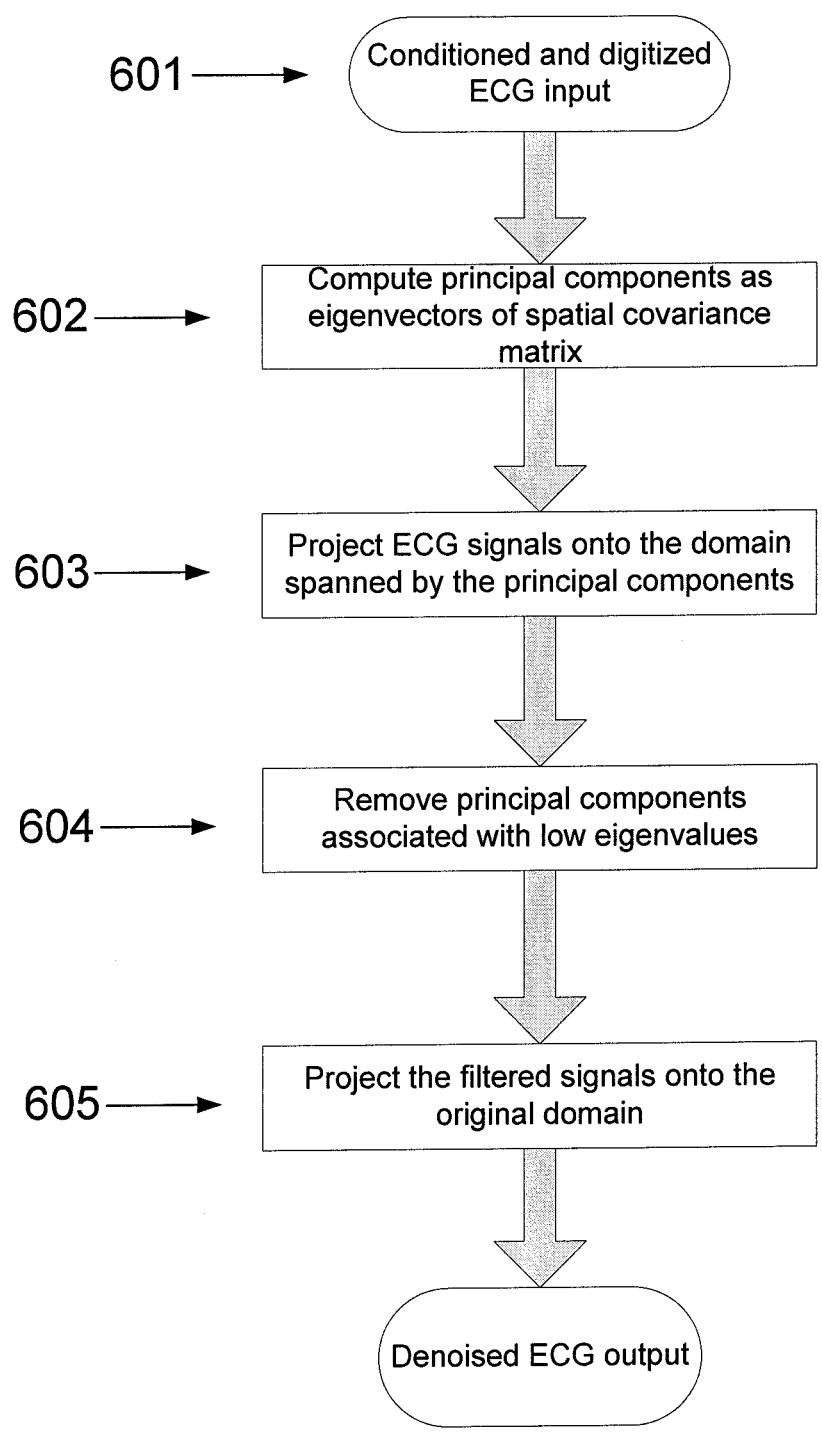
FIG. 6 shows a signal flow diagram of a principal component analysis denoising algorithm as implemented in a denoising module, consistent with an example embodiment of the present invention.

In another embodiment, and referring to FIG. 6, the digitized ECG signal 601 is denoised using principal component analysis (PCA). In this embodiment the multi-channel ECG signal is projected onto the domain of its principal components [7]. The principal components are computed in process 602 by performing eigenvalue or singular value decomposition of the spatial covariance matrix computed from ECG signals. The projection of ECG signals onto the domain of their principal components is performed in process 603 by multiplying the ECG signals by the extracted unitary matrix of eigenvectors or singular vectors. This linear projection results in new signals that are uncorrelated with normalized variance. Geometrically, the projection involves rotation and scaling of the data in order to orthogonalize signal components. Among the orthogonalized components, the ones with low signal power are often associated with noise and can be removed to achieve denoising. The data are filtered by zeroing the principal components associated with smaller eigenvalues in process 604. In one embodiment the filtered data can be projected back onto the original domain at 605 using the unitary matrix of eigenvectors to retain original signal morphology.

In one embodiment PCA is performed in combination with independent component analysis technique (ICA) [8] for denoising. In this embodiment, PCA is performed as a preliminary step to decorrelate the signals prior to applying ICA for noise removal. In various embodiments involving the use of an ICA technique for denoising the signal, noise sources are separated by achieving their mutual independence. In one embodiment the problem of maximizing independence of ECG recording from contaminating noise is found as a solution of an optimization problem that maximizes independence between the signal sources. For example, ICA techniques can use either higher-order statistics of signal components [9, 10] or information-theoretic criteria to maximize independence. Information-theoretic criteria that can be applied include maximization of negentropy or its approximation [11], minimization of mutual information [11], maximum likelihood estimation [12, 13], maximum a posteriori probability [14], or expectation—maximization of Gaussian mixture models of sources [15]. These solutions can be approximated via efficient numerical methods, such as FastICA [16] and JADE [11] algorithms.

In some embodiments, it is useful to compute signal-to-noise ratio (SNR) of the input signal 601 when denoising using PCA. The parameters required in Formula 1, $P_{signal}$ and $P_{noise}$, can be computed as a byproduct of the PCA denoising process. $P_{signal}$ can be estimated as the sum of the eigenvalues of the retained principal components in process 604. Likewise, $P_{noise}$ can be estimated as the sum of the eigenvalues of the principal components removed in process 604.

Figure 7:
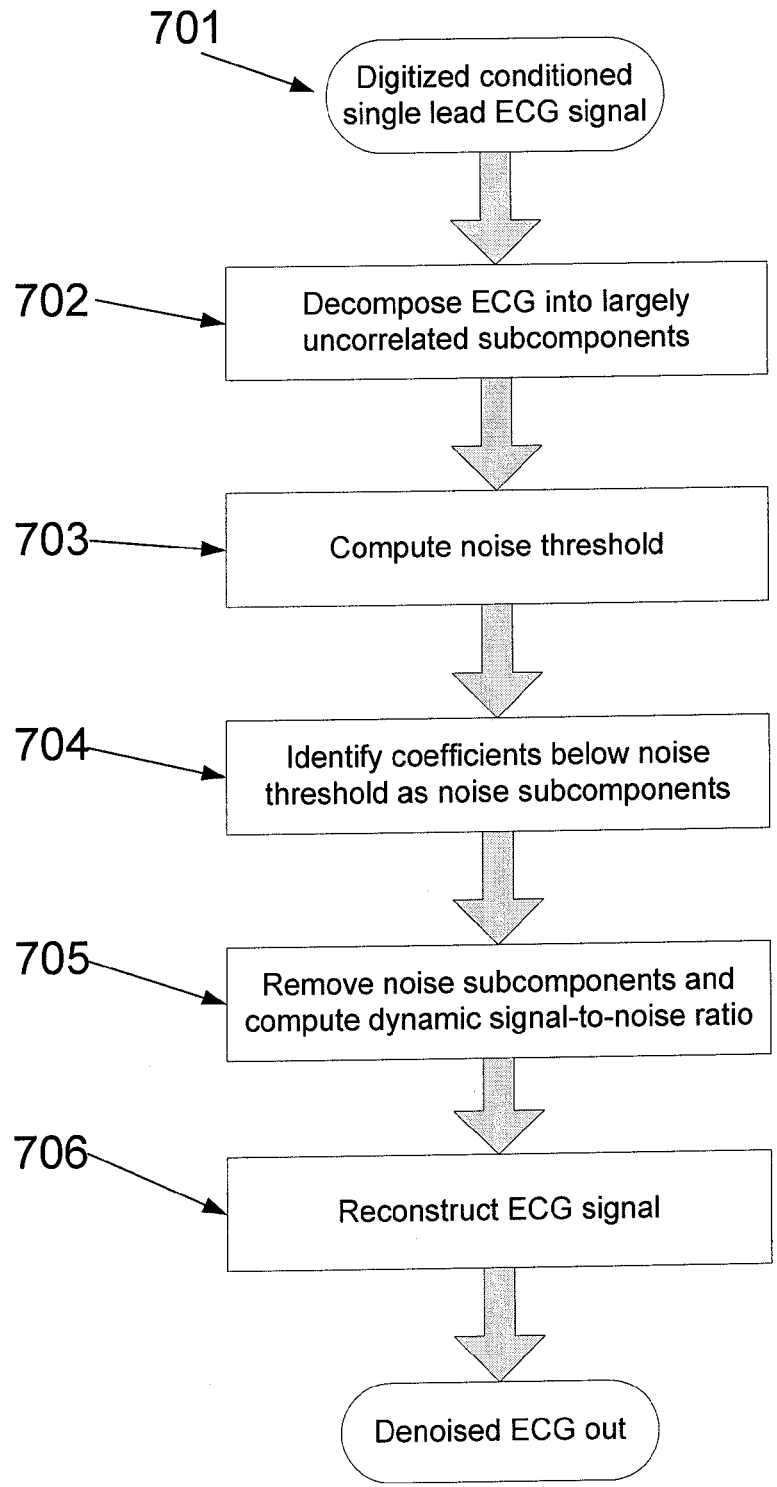
FIG. 7 shows a signal flow diagram of the decomposition and thresholding denoising algorithm as implemented in a denoising module, consistent with an example embodiment of the present invention.

In another embodiment, and referring to FIG. 7, the digitized ECG signal 701 is denoised using a signal decomposition and thresholding technique (SDTT), in accordance with another example embodiment of the present invention. In process 702 input signal 701 is decomposed into subcomponents in a second domain of larger dimension than the first domain. The dimension of the first domain is defined by the number of observed, or captured, signal channels. The dimension of the second domain is defined by the number of channels multiplied by the number of subcomponents in each channel. Decomposition step 702 is performed using one of a variety of transforms that result in a small signal reconstruction error. Such transforms may include, for example, a discrete cosine transform [17], a wavelet related transform [19], a Karhunen-Loeve transform [21], a Fourier transform [18], a Gabor transform [20], or a filter bank [19]. In one embodiment, denoising is facilitated by a decomposition whereby signal energy is concentrated in a small number of large subcomponent coefficients, while noise is spread out across either many decomposition levels or decomposition levels corresponding to higher frequency and is represented by small coefficients. In process 705, the signal quality is enhanced by discarding subcomponents below a threshold computed in process 703. The energy in the discarded subcomponents is used to estimate noise energy in process 705. Signal energy, for computing SNR in process 705 is estimated using the residual subcomponents representing the denoised ECG signal. SNR is computed from noise energy and signal energy estimates as described herein. In some implementations, instead of discarding subcomponents below a threshold, those subcomponents above a threshold (the residual subcomponents above) can be positively identified and used to estimate the signal energy, with the remaining energy being noise. Techniques similar to soft or hard thresholding [23] can be used to remove this noise in process 704. Examples of a threshold selection rule used to compute the noise threshold in process 703 include adaptive threshold selection using the principle of Stein's Unbiased Risk Estimate and fixed threshold based on signal statistics such as SD*sqrt(2*log(length (X)), where SD is standard deviation and X is a vector of subcomponents [22]. The residual subcomponents are combined in process 706 to reconstruct an ECG signal using the inverse of the transform used for signal decomposition in process 702.

Figure 8:
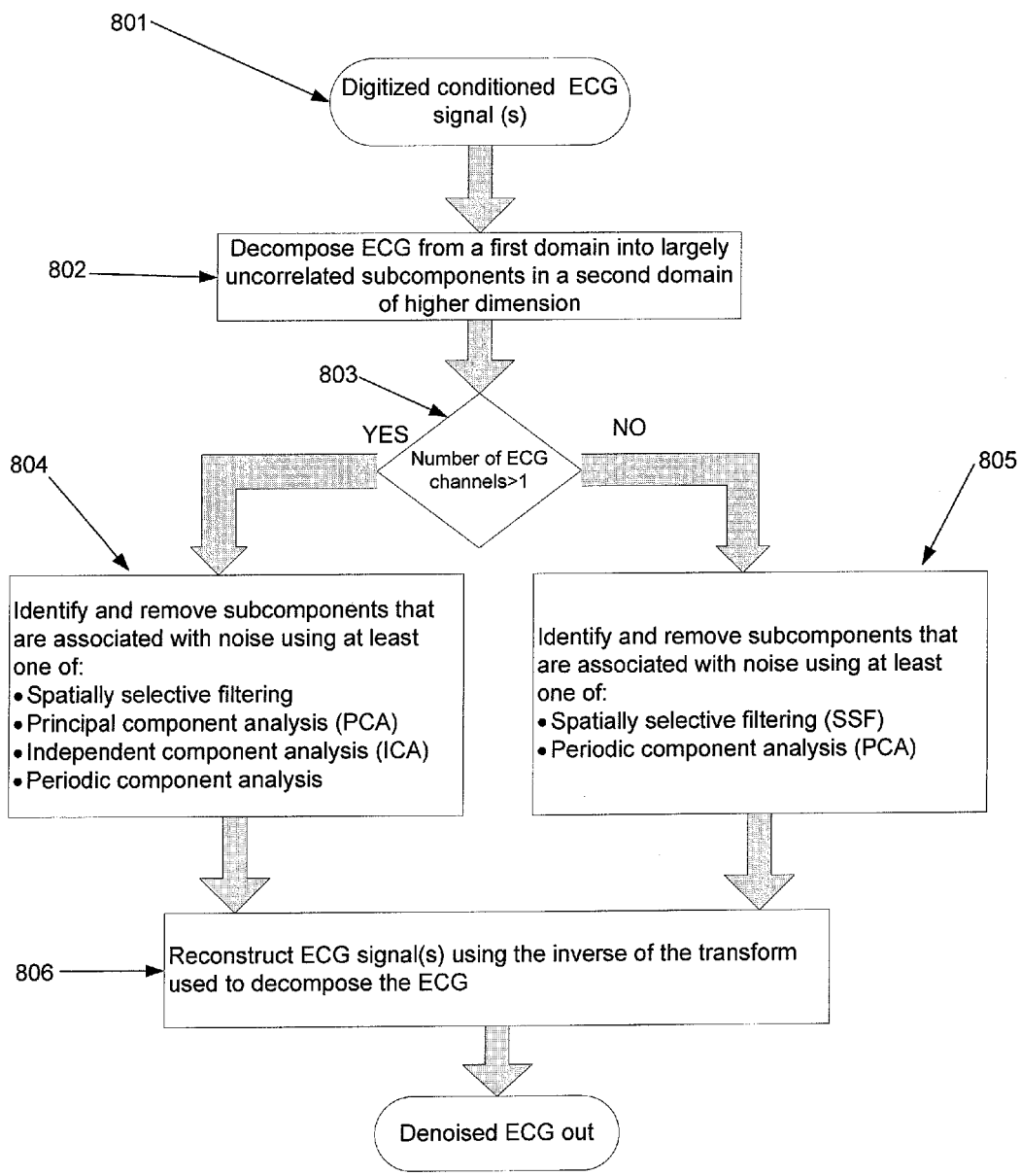
FIG. 8 shows a signal flow diagram of a Multi-Domain Signal Processing (MDSP) denoising algorithm as implemented in the denoising module, consistent with an example embodiment of the present invention.

Referring to FIG. 8, the digitized ECG is denoised using an MDSP embodiment. Input signal 801 is decomposed in process 802 from a first domain into largely uncorrelated subcomponents in a second domain of higher dimension. Decomposition in process 802 is accomplished using one of a discrete cosine transform, a Karhunen-Loeve transform, a Fourier transform, a Gabor transform, and a filter bank. In another embodiment, decomposition is accomplished using a wavelet-related transform and the decomposition levels correspond to wavelet scales. In another embodiment, decomposition is achieved by representing the observed signals as a linear combination of basis functions. Signal decomposition embodiments and the use of subcomponents derived from the decomposition for denoising (removal of at least some of the in-band noise contained in the signal), extraction of information from the signal, and evaluation of the accuracy of extracted information is referred to as Multi-Domain Signal Processing (MDSP) by way of example, in the discussion herein. Use of MDSP techniques for removal of in-band noise from a signal is referred to as Multi-Domain Filtering (MDF).

The dimension of the first domain is defined by the number of ECG channels. The dimension of the second domain is defined by the number of channels multiplied by the number of subcomponents in each channel. Following decomposition, signal flow is directed to either process 804 or 805 by decision point 803, depending upon the number of channels in the signal. If the ECG signal has only one channel, signal flow is directed to process 805, where either spatially selective filtering (SSF) [24, 28, 29] or periodic component analysis [25, 26] are used alone or in combination to identify subcomponents that contain more noise energy than signal energy. If the ECG signal has more than one channel, signal flow is directed to process 804, where either spatially selective filtering, principal component analysis [27], independent component analysis, or periodic component analysis are used either alone or in combination to identify subcomponents that contain more noise energy than signal energy. A subcomponent that contains more noise than signal energy is said to be associated with noise. Conversely, a subcomponent that contains more signal energy than noise energy is said to be associated with a signal.

In some embodiments, processes 804 and 805 result in separation of subcomponents into two groups, one associated with noise and the other associated with the ECG signal. Determining whether a subcomponent is associated with noise or ECG signal within a targeted interval of time is accomplished by using one or more of principal component analysis (PCA), independent component analysis (ICA), periodic component analysis (πCA) and spatially selective filtering (SSF). PCA and ICA are applicable to multi-lead ECG, while πCA and SSF can be applied to either multi-lead or single-lead ECG.

The PCA technique [7,27] employed in processes 804 and 805 uses subcomponent covariance information to orthogonalize subcomponents. The orthogonalized subcomponents with low signal power are often associated with noise and can be removed to achieve denoising. PCA can be used as a preliminary step prior to applying an ICA technique. The ICA technique further separates signal and noise sources [8] as a solution of an optimization problem that maximizes independence between them. The πCA technique computes and jointly diagonalizes covariance and autocorrelation matrices of subcomponents to separate them based on their periodicity or quasi-periodicity [25, 26]. The πCA technique extracts most periodic subcomponents corresponding to ECG rhythm and, since noise is not generally periodic, it is left behind.

SSF techniques [24, 28, 29] employed in processes 804 and 805 detect one or more signal-related features (e.g., QRS complex) and pass them across the subcomponents while blocking features inherent to noise. The technique relies on the differences of noise and signal distributions across decomposition levels. In one embodiment, spatially selective filtering is facilitated by a decomposition whereby signal energy is concentrated in a small number of large subcomponent coefficients while noise is spread out across many decomposition levels and is represented by small coefficients. Techniques similar to wavelet thresholding [23] can be used to remove this noise.

In another embodiment of process 804 and 805, a spatially selective filtering approach exploits the fact that most noise subcomponents are confined to decomposition levels that represent high frequencies. In this embodiment the locations of signal features are identified by examining subcomponents corresponding to lower frequency. For example, a QRS wave location can be identified as high amplitude changes in peaks and valleys that occur simultaneously across multiple subcomponents associated with lower frequencies. To avoid signal distortion, the subcomponents associated with high frequency are preserved within the time window surrounding the identified peaks and valleys, and are zeroed at other times. By zeroing out the subcomponents or time segments within subcomponents associated with noise, and reconstructing the ECG signal using those subcomponents associated with the ECG signal, the in-band noise level in the ECG is reduced, or "denoised", to create a denoised ECG.

The subcomponents identified as associated with noise in processes 804 and 805 are removed and the residual subcomponents are used to reconstruct a denoised ECG signal for each ECG channel in process 806 using the inverse of the transform used to decompose the ECG in process 802. In some implementations, instead of removing subcomponents that are associated with noise, subcomponents associated with signal energy are identified (the residual subcomponents above) and used to estimate the signal energy, with the remaining energy being noise.

In some embodiments involving an MDSP-based approach, a signal-to-noise ratio (dSNR) is computed as the ratio of the energies in signal and noise subcomponents. In one embodiment, referring to FIG. 8, following separation of subcomponents into two groups, as described herein in processes 804 and 805, the power in each of the groups, $P_{signal}$ and $P_{noise}$, is independently computed and used to compute SNR as per formula 1.

Figure 9:
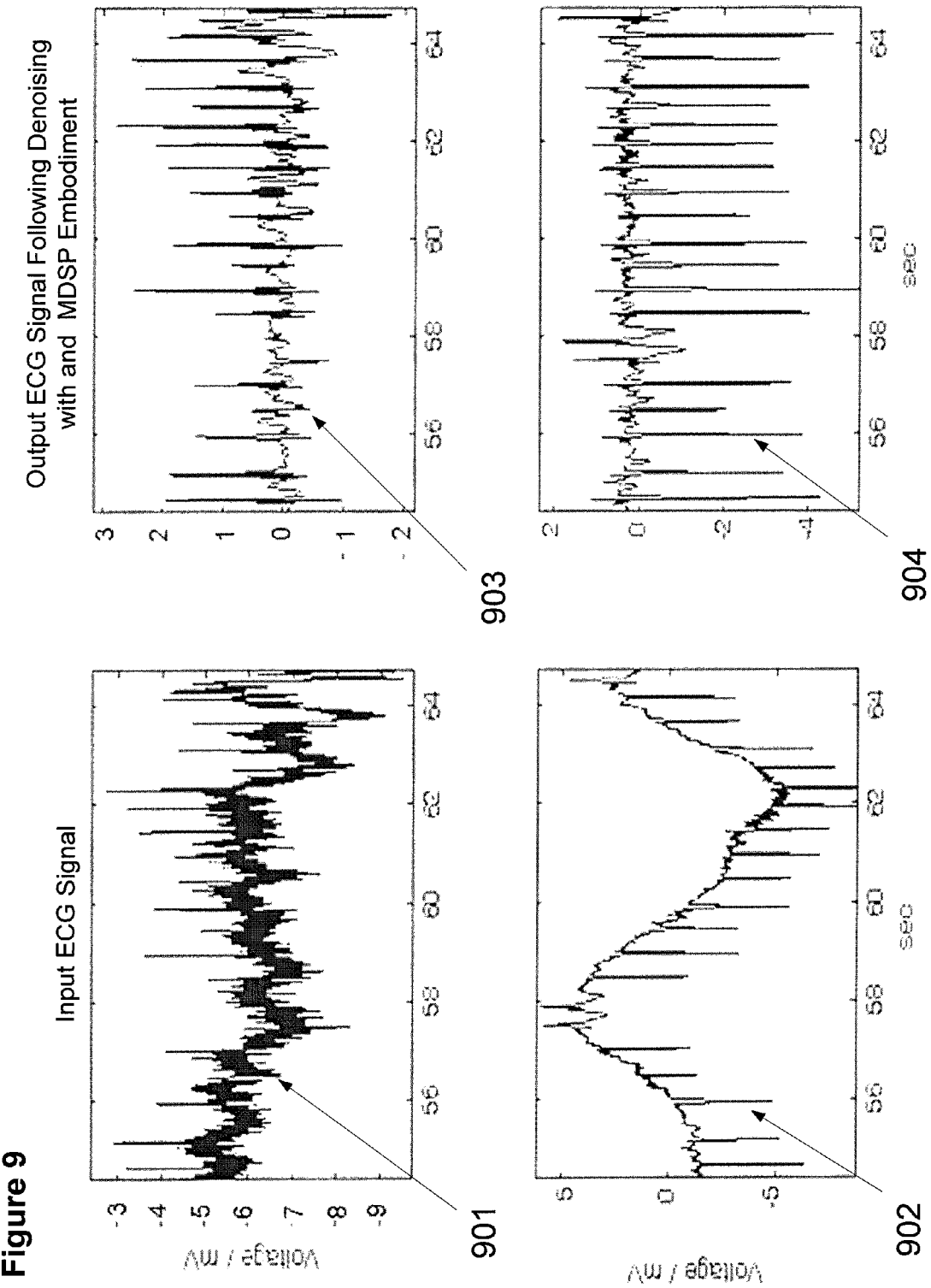
FIG. 9 shows an example of a two-lead ECG signal that has been denoised using an MDSP embodiment, consistent with an example embodiment of the present invention.

Referring to FIG. 9, an example of a two channel ECG signal denoised by an MDSP embodiment is provided. Input signals 901 and 902 are recordings of a human ambulatory ECG and were obtained from the MIT-BIH database. Output ECG traces 903 and 904 are shown for each channel. The improvement in SNR in this example is approximately 8 dB and noise amplitude is reduced by about 85% with no noticeable distortion.

Figure 10:
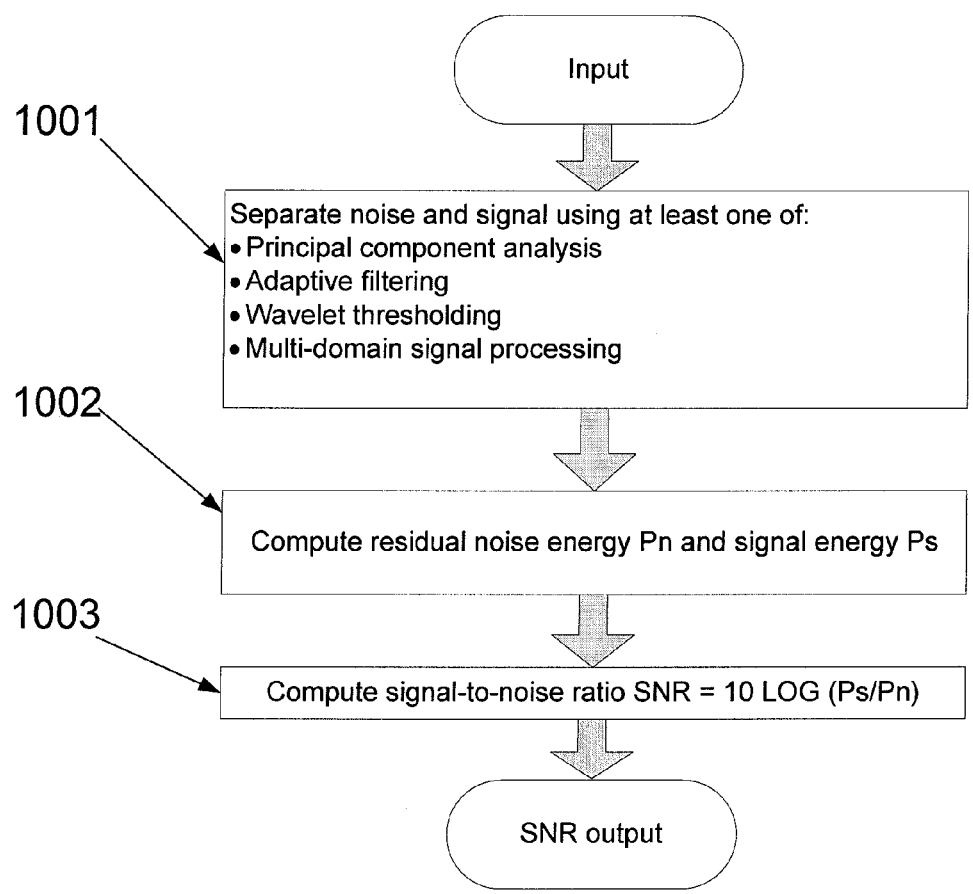
FIG. 10 shows a signal flow diagram for computing a signal-to-noise ratio for an ECG signal, consistent with an example embodiment of the present invention.

In some embodiments, and referring to FIG. 10, signal-to-noise ratio is computed for evaluating signal quality. As described herein, a measure of signal quality can be useful to change the effective source impedance of the ECG signal communicated to the ambulatory monitoring device when the device is configured to detect unusually high source impedance as an indicator that an ECG sensing electrode is in poor contact with the skin. In process 1001, signal and noise are separated. Some embodiments for separating signal and noise, described herein, include adaptive filtering, decomposition and thresholding, principal component analysis, and MDSP denoising embodiments. In process 1002, separated noise and signal are used to estimate signal energy and noise energy. SNR is computed in process 1003, as described herein. The approach used in process 1001 to separate signal and noise would typically match the process technique used for denoising, as the signal and noise values can be computed as a byproduct of the denoising process. Hence the technique used in 1001 will depend upon the method of denoising.

Various embodiments as described herein can be used in connection with ambulatory monitoring devices. For instance, devices as discussed herein can be used as a substitute for existing passive ECG leads used with ambulatory monitoring devices, such as Holter monitors, event recorders, and Mobile Cardiac Outpatient Telemetry devices. Such devices may be used, for example, to improve performance of these devices in one or more of a variety of manners.

In some embodiments, denoising module 200 includes a wireless communication link to communicate the denoised ECG to a location away from the body of the subject from which the ECG is obtained.

The various computing components, circuits and signal processing methods described herein can be implemented using a variety of devices and methods. For example, computing, logic or processing circuits can be implemented using one or more of: discrete logic circuitry, fully-programmable and semi-programmable circuits such as PLAs (programmable logic arrays), specialized processors or general purpose processors that are specially programmed. Combinations of these and other circuit components are also possible and within the scope of various embodiments, including those discussed above. For example, the various components and processes shown in the figures can be implemented in a variety of circuit-based forms, such as through the use of data processing circuit modules. Such systems are exemplified by implementation in high-speed programmable computer/processor circuits, or in combination with discrete and or semi-programmable circuitry (e.g., as Field-Programmable Gate Arrays, Programmable Logic Devices/Arrays).

REFERENCES CITED

For general information regarding a variety of fields that may relate to one or more embodiments of the present invention, and for specific information regarding the application of one or more such embodiments, reference may be made to the following documents, which are fully incorporated herein by reference.

Various ones of these references are further cited above via corresponding numerals, and may be implemented as such.
1. Akinori Ueno, et al. Capacitive sensing of electrocardiographic potential through cloth from the dorsal surface of the body in a supine position: a preliminary study. IEEE Transactions on Biomedical Engineering, vol. 54, no. 4, April 2007, pp 759-766
4. N. V. Thakor and Y. Zhu, "Applications of adaptive filtering to ECG analysis: noise Cancellation and arrhythmia detection," IEEE Trans. Biomedical Engineering, Vol. 38, No. 8, pp. 785-794, August 1991.
5. B. Widrow, et al., "Adaptive noise cancelling: principles and applications," IEEE Proc., Vol. 63, No. 12, pp. 1692-1716, December 1975.
6. S. Hadei, M. lotfizad. A family of adaptive filter algorithms in noise cancellation for speech enhancement. International Journal of Computer and Electrical Engineering, Vol. 2, No. 2, April 2010. 1793-8163
7. L. Smith A tutorial on Principal Components Analysis, http://users.ecs.soton.ac.uk/hbr03r/pa037042.pdf
8. P. Comon, "Independent component analysis, a new concept?," Signal Process. Special Issue on Higher Order Statistics, vol. 36, no. 3, pp. 287-314, 1994.
9. J.-F. Cardoso, "High-order contrasts for independent component analysis," Neural Comput., vol. 11, no. 1, pp. 157-192, 1999.
10. Blaschke, T.; Wiskott, L.; CuBICA: independent component analysis by simultaneous third- and fourth-order cumulant diagonalization IEEE Transactions on Signal Processing, Volume 52, Issue 5, May 2004 Page(s):1250-1256
11. Hyvärinen, A. New approximations of differential entropy for independent component analysis and projection pursuit. In *Advances in Neural Information Processing Systems*, volume 10, pages 273-279. MIT Press.
12. Bell, A. and Sejnowski, T., An information-maximization approach to blind separation and blind deconvolution, *Neural Computation,* 7:1129-1159.
13. Cardoso, J.-F. Infomax and maximum likelihood for source separation. *IEEE Letters on Signal Processing,* 1997, 4, 112-114.
14. M. Zibulevsky, B. Pearlmutter, Blind source separation by sparse decomposition in a signal dictionary, Neural Computation 2001, v13, pp 863-882.
15. Todros, K.; Tabrikian, J.; Blind Separation of Independent Sources Using Gaussian Mixture Model IEEE Transactions on Signal Processing Volume 55, Issue 7, Part 2, July 2007 Page(s):3645-3658
16. Hyvärinen, A. Fast and robust fixed-point algorithms for independent component analysis. *IEEE Transactions on Neural Networks,* 10(3):626-634.
17. K. R. Rao and P. Yip, Discrete Cosine Transform: Algorithms, Advantages, Applications San Diego, Calif.: Academic, 1990.
18. Mallat, S. G., and Zhang, Z., Matching Pursuits with Time-Frequency Dictionaries, IEEE TSP (41), No. 12, December 1993, pp. 3397-3415.
19. Vaidyanathan, Multirate Systems and Filter Banks, Prentice Hall, 1993
20. J. Woods. Subband Coding, Kluwer Academic Press, 1990.
21. K. S. Ball, L. Sirovich, L. R. Keefe, Dynamical eigenfunction decomposition of turbulent channel flow. International Journal for Numerical Methods in Fluids Volume 12, Issue 6, Date: 5 Apr. 1991, Pages: 585-604
22. Donoho, D. L., I. M. Johnstone (1994), "Ideal spatial adaptation by wavelet shrinkage," Biometrika, vol 81, pp. 425-455.
23. Donoho, D. L. (1995), "De-noising by soft-thresholding," IEEE Trans. on Inf. Theory, 41, 3, pp. 613-627.
24. Xu, Yansun, et. al. Wavelet transform domain filters: a spatially selective noise filtration technique, IEEE transactions on image processing 1994, vol. 3, no 6, pp. 747-758
25. L. K. Saul and J. B. Allen, "Periodic component analysis: An eigenvalue method for representing periodic structure in speech.," in NIPS, [Online] 2000, pp. 807-813. Available: http://www.cs.cmu.edu/Groups/NIPS/00papers-pub-on-web/SaulAllen.pdf
26. R Sameni, et. al. Multichannel electrocardiogram decomposition using periodic component analysis. IEEE Transactions on Biomedical Engineering, 2008 vol 55, no 8 pp 1935-1940
27. Aminghafari, M.; Cheze, N.; Poggi, J-M. (2006), "Multivariate de-noising using wavelets and principal component analysis," *Computational Statistics & Data Analysis*, 50, pp. 2381-2398
28. Mallat, S. G., Hwang, W. L., Singularity Detection and Processing with Wavelets, IEEE Transactions on Information Technology (38), 1991, pp. 617-643.
29. Pan Q., Zhang L. Dai G. and et al. Two denoising methods by wavelet transform. IEEE Trans. on SP., 1999, 47(12): 3401-3406

Based upon the above discussion and illustrations, those skilled in the art will readily recognize that various modifications and changes may be made to the present invention without strictly following the exemplary embodiments and applications illustrated and described herein. For exam, various aspects are directed to signal processing such as denoising using one or more approaches as described in one or more of the priority documents referenced above and incorporated herein. One such aspect involves the denoising of an ECG signal using one or more approaches described in connection with multi-domain signal processing as described in these documents. Such modifications and changes may include, for example, incorporating one or more aspects described in the above references and/or applying one or more embodiments thereto, or combining embodiments. These and other modifications do not depart from the true spirit and scope of the present invention, including that set forth in the following claims.

What is claimed is:
1. An apparatus for wearing on a body of a live being, the apparatus comprising:
   a battery;
   at least two electrodes configured and arranged to sense an ECG signal from the live being;
   a denoising module powered by the battery, communicatively coupled to the at least two electrodes and configured and arranged to receive the ECG signal sensed by the sensing electrodes, the denoising module including circuitry configured and arranged to digitize the ECG signal, and a computing circuit configured and arranged to process said digitized ECG signal to denoise the digitized ECG signal by increasing a signal-to-noise ratio in the ECG signal by at least 15 dB, and reconstruct the ECG signal with a quality of signal reconstruction of at least 95%; and a communications circuit powered by the battery and configured and arranged to generate a communication including the reconstructed ECG signal for access by a device remote from the communications circuit.

2. The apparatus of claim 1, wherein the electrodes are dry electrodes.

3. The apparatus of claim 1, wherein the computing circuit is configured and arranged to process said digitized ECG signal to reduce in-band noise using multi-domain signal processing.

4. The apparatus of claim 3, wherein the computing circuit is configured and arranged to process said digitized ECG signal to reduce in-band noise using principal component analysis.

5. The apparatus of claim 1, wherein the computing circuit is configured and arranged to denoise the digitized ECG signal by decomposing the digitized ECG signal from a first domain into subcomponents in a second domain, identify a signal subcomponent in a time segment based upon characteristic frequency content of an ECG in said time segment of a cardiac cycle, and reconstruct the ECG signal by constructing a denoised ECG signal in the first domain from at least two subcomponents identified as signal subcomponents.

6. The apparatus of claim 1, wherein the computing circuit is configured and arranged to denoise the digitized ECG signal based upon a time-based distribution of subcomponents resulting from decomposition of the signal.

7. The apparatus of claim 1, wherein the communications circuit is integrated with the denoising module in a chip, and the at least two electrodes are directly connected to the chip via a conductive lead, the chip being configured and arranged for wearing by a human and to generate the communication via the communications circuit by generating and transmitting a wireless signal for access by a device remote from the chip.

8. The apparatus of claim 1, wherein the ECG signal has a 3 dB bandwidth of at least 40 Hz.

9. The apparatus of claim 1, wherein the apparatus has a volume of less than 15 cc.

10. The apparatus of claim 1, wherein the computing circuit is configured and arranged to increase the signal-to-noise ratio in the ECG signal by at least 25 dB.

11. The apparatus of claim 1, wherein the ECG signal is a simulated ECG signal, synthesized according to the ANSI EC57 standard for purposes of measuring the signal-to-noise ratio, and the signal-to-noise ratio of the sensed signal is between 0 and 30 dB.

12. An apparatus comprising:

at least two electrodes configured and arranged to sense an ECG signal;

a denoising module communicatively coupled to the at least two electrodes and configured and arranged to receive the ECG signal sensed by the sensing electrodes, the denoising module including circuitry configured and arranged to condition and digitize the ECG signal, and a computing circuit configured and arranged to denoise process said digitized ECG signal by decomposing the digitized ECG signal from a first domain into subcomponents in a second domain, identifying subcomponents that are associated with noise based upon a spatial distribution of the subcomponents, and constructing a denoised physiological signal in the first domain from at least two of the subcomponents that have not been identified as being associated with noise; and a communications circuit configured and arranged to generate a communication including the denoised ECG signal for access by a device remote from the communications circuit.

13. The apparatus of claim 12 wherein identifying subcomponents based upon spatial distribution includes spatially selective-filtering the subcomponents.

14. The apparatus of claim 12, wherein identifying subcomponents based upon spatial distribution includes identifying the subcomponents using principal component analysis.

15. The apparatus of claim 12, wherein the computing circuit is configured and arranged to identify subcomponents that are associated with noise by identifying signal subcomponents as subcomponents having more signal energy than noise energy, and identifying noise subcomponents within a time segment of the ECG signal as subcomponents that are not the signal subcomponents.

16. The apparatus of claim 12, wherein the computing circuit is configured and arranged to identify subcomponents that are associated with noise by identifying at least one time segment of the ECG signal as being associated with noise based upon frequency content of a representative ECG signal, and identifying subcomponents falling within the at least one time segment as subcomponents that are associated with noise.

* * * * *

UNITED STATES PATENT AND TRADEMARK OFFICE
CERTIFICATE OF CORRECTION

| | | |
|---|---|---|
| PATENT NO. | : 8,543,195 B1 | Page 1 of 1 |
| APPLICATION NO. | : 13/293632 | |
| DATED | : September 24, 2013 | |
| INVENTOR(S) | : Brockway et al. | |

It is certified that error appears in the above-identified patent and that said Letters Patent is hereby corrected as shown below:

In the Claims

Col. 14, line 15, Claim 12: "denoise process said" should read --denoise said--.

Signed and Sealed this
Tenth Day of February, 2015

Michelle K. Lee
*Deputy Director of the United States Patent and Trademark Office*